(12) United States Patent
Williams (10) Patent No.: US 7,534,228 B2
(45) Date of Patent: May 19, 2009

(54) BRIDLE CATHETER WITH UMBILICAL TAPE

(75) Inventor: Derek M. Williams, Cuyahoga Falls, OH (US)

(73) Assignee: Applied Medical Technology, Inc., Brecksville, OH (US)

( * ) Notice: Subject to any disclaimer, the term of this patent is extended or adjusted under 35 U.S.C. 154(b) by 733 days.

(21) Appl. No.: 11/113,471

(22) Filed: Apr. 25, 2005

(65) Prior Publication Data
US 2005/0236001 A1 Oct. 27, 2005

Related U.S. Application Data

(60) Provisional application No. 60/565,580, filed on Apr. 27, 2004.

(51) Int. Cl.
*A61M 1/00* (2006.01)
(52) U.S. Cl. .................. 604/174; 604/27; 604/179; 604/180; 604/264; 128/200.24; 128/200.26; 128/207.18
(58) Field of Classification Search ............. 604/28, 604/174, 180; 126/206.11, 207.14; 128/200.24, 128/203.22
See application file for complete search history.

(56) References Cited

U.S. PATENT DOCUMENTS

| 3,420,237 | A | * | 1/1969 | Fortay, et al. ............. 601/11 |
| 4,114,626 | A | | 9/1978 | Beran |
| 4,282,871 | A | | 8/1981 | Chodorow et al. |
| 4,318,404 | A | * | 3/1982 | Cunningham .............. 604/12 |
| 4,778,448 | A | | 10/1988 | Meer |
| 4,790,809 | A | * | 12/1988 | Kuntz ..................... 604/8 |
| 4,823,789 | A | | 4/1989 | Beisang, III |
| 5,021,043 | A | * | 6/1991 | Becker et al. ............. 606/192 |
| 5,097,827 | A | | 3/1992 | Izumi |
| 5,105,807 | A | | 4/1992 | Kahn et al. |
| 5,117,818 | A | | 6/1992 | Palfy |
| 5,185,005 | A | | 2/1993 | Ballantyne |
| 5,492,538 | A | | 2/1996 | Johlin, Jr. |
| 5,735,272 | A | | 4/1998 | Dillon et al. |
| 5,851,185 | A | * | 12/1998 | Berns ..................... 600/434 |
| 6,248,092 | B1 | * | 6/2001 | Miraki et al. ............ 604/96.01 |
| 6,355,050 | B1 | * | 3/2002 | Andreas et al. ........... 606/144 |
| 6,464,668 | B1 | * | 10/2002 | Pace ..................... 604/179 |
| 6,478,026 | B1 | | 11/2002 | Wood |
| 6,631,715 | B2 | | 10/2003 | Kirn |
| 6,837,237 | B2 | | 1/2005 | Kirn |
| 2002/0088905 | A1 | * | 7/2002 | Hansen .................... 248/65 |
| 2004/0069309 | A1 | * | 4/2004 | Kirn ...................... 128/207.8 |

* cited by examiner

*Primary Examiner*—Nicholas D Lucchesi
*Assistant Examiner*—Scott Medway
(74) *Attorney, Agent, or Firm*—Pearne & Gordon LLP

(57) ABSTRACT

A nasal tube retaining system having a flexible member with a magnet attached to the first end for insertion into the first nostril of the patient, a tape portion attached to an end of the flexible member, a guide for guiding the tape portion through a portion or all of the flexible member, a rod, and a retrieving member with a magnetic distal end for insertion into the second nostril of the patient to retrieve the flexible member. The system further includes a fastening means to secure the nasal tube to the tape portion.

16 Claims, 6 Drawing Sheets

BRIDLE CATHETER WITH UMBILICAL TAPE

FIELD OF INVENTION

The present invention relates to a nasal tube retaining system and more specifically to a method for packaging such a retaining system and placing the retaining system in the nasal passage of a patient to secure nasal tubes.

BACKGROUND OF THE INVENTION

In an effort to prevent premature pullouts, nasoenteric tubes are often fixed in place using a wide variety of bridling systems. Most of these systems are difficult to place in the patient, requiring great dexterity by the physician and present unusual discomfort for the patient. Other bridling systems have additional disadvantages such as the bridle system disclosed in U.S. Pat. No. 6,631,715 to Kirn. Kirn uses a flexible tube like member as the bridle for securing the nasal tube. In the preferred embodiment the flexible member having a magnetic end is inserted into the first nare of the patient and a magnetic probe is inserted into the second nare of the patient. Both the flexible member and magnetic probe are inserted just beyond the posterior border of the nasal septum. The magnetic probe retrieves the flexible member thereby looping the flexible member around the nasal septum. The flexible member remains in the patient thereby forming the bridle. Once the magnetic end of the flexible member is trimmed away both ends of the flexible member and the nasal tube are inserted into channels of a receiver thereby securing the nasal tube to the flexible member or bridle. A disadvantage to this type of bridle is that the flexible member will begin to stretch causing the diameter to decrease. As the diameter decreases the flexible member becomes dislodged from the channels of the receiver and therefore does not stay in place to secure the nasal tube.

Another type of bridle system is disclosed in U.S. Pat. No. 5,185,005 to Ballantyne. Ballantyne utilizes two magnetic insertion tools to place a bridle around the posterior nasal septum of the patient. A first insertion tool with the bridle attached is inserted into the first nostril and a second insertion tool is inserted into the second nostril of the patient until they magnetically couple behind the posterior nasal septum. Once coupled the first insertion tool is removed from the first nostril leaving the bridle coupled to the second insertion tool. The second insertion tool is then removed from the second nostril thereby pulling the bridle through the first nostril around the posterior nasal septum and out the second nostril. The disadvantage of Ballantyne is that the insertion tools consist of several unnecessary parts, such as installation tool 34 and bridle 10, that must telescope relative to each other during removal of the installation tool, a pulling cord that serves no other purpose, and a fastening plate requiring a countersunk drilled hole. These additional parts are both difficult to manufacture and time consuming to assemble. This leads to increased manufacturing costs and more opportunities for defects.

Another type of bridle system is disclosed in U.S. Pat. No. 4,778,448 to Meer. In the preferred embodiment both ends of the bridle are inserted into separate nostrils until they are present in the hypopharynx. Each end of the bridle is then extracted through the mouth of the patient using forceps. The ends of the bridle are secured together thereby forming a loop. The portion of the bridle extending out of the second nostril is then pulled so that the secured ends are pulled back through the mouth until the loop portion is contacts the posterior aspect of the nasal septum. The disadvantage of the Meer bridle system is that the time to place the bridle is time consuming and is uncomfortable for the patient.

Additional bridle systems for securing a nasal tube include attaching the tubes directly to the skin of the patient using an adhesive as described in U.S. Pat. No. 5,735,272 to Dillion et al., U.S. Pat. No. 4,823,789 to Beisang, III and U.S. Pat. No. 4,114,626 to Beran. The disadvantage to this type of system is that the adhesive is uncomfortable to the patient and can cause skin irritation. Furthermore, the adhesive will gradually lose its adhesion over time thereby becoming dislodged.

Another type of bridle system are those disclosed in U.S. Pat. No. 5,117,818 to Palfy and U.S. Pat. No. 4,282,871 to Chodorow et al. This type of system uses a harness that wraps around the patients head or behind the patients ears. The disadvantage to this type is that the harness can become easily dislodged accidentally or be easily removed by an uncooperative patient.

Therefore, there exists a need to provide a bridle system to overcome the aforementioned disadvantages and provide a system that is cost effective, easy to manufacture and easily and rapidly placed in the patient with minimal discomfort.

BRIEF SUMMARY OF THE INVENTION

The present invention overcomes the aforementioned disadvantages by providing in one aspect a nasal tube retaining system comprising a flexible member having a first and second end, wherein the first end is inserted into a first nostril of a patient, a magnet operatively attached in the first end of the flexible member, a tape portion having a first and second end, wherein the tape portion is operatively attached to the flexible member, a retrieving member having a magnetic distal end, wherein the distal end is inserted into a second nostril of the patient, wherein the distal end of the retrieving member attracts the first end of the flexible member to retrieve and remove the flexible member, and a fastening means to secure at least one nasal tube and the first and second ends of the tape portion.

In accordance with another aspect of the present invention a method of placing a nasal tube retaining system into a patient is disclosed and comprises the steps of providing a flexible member having a first and second end, a magnet operatively attached in the first end of the flexible member, a tape portion having a first and second end, wherein the tape portion is operatively attached to the flexible member, a rod inserted into the flexible member, a retrieving member having a magnetic distal end, inserting the first end of the flexible member into a first nostril of the patient, extending the flexible member down to the posterior nasopharynx, inserting the distal end of the retrieving member into a second nostril of the patient, extending the retrieving member down to the posterior nasopharynx thereby permitting the first end of the flexible member and the distal end of the retrieving member to magnetically connect, removing the rod from the flexible member, pulling the retrieving member out of the second nostril thereby removing the flexible member until the flexible member is completely removed from the patient leaving only the tape portion remaining in the patient, cutting the flexible member, and removing the flexible member from the tape portion.

In accordance with yet another aspect of the present invention a method of packaging a nasal tube retaining system is disclosed that comprises the steps of providing a flexible member having a first and second end, a magnet for attachment in the first end of the flexible member, a tape portion having a first and second end, and a tube stretcher, stretching the first end of the flexible member, inserting the magnet into the first end of the flexible member, securing the magnet in the first end of the flexible member, and securing the tape portion to the flexible member.

Additional benefits and advantages of the present invention will become apparent to those skilled in the art to which it pertains upon a reading and understanding of the following detailed specification.

BRIEF DESCRIPTION OF THE DRAWINGS

The invention may take physical form in certain parts and arrangement of parts, a preferred embodiment of which will be described in detail in this specification and illustrated in the accompanying drawings that form a part of the specification.

DETAILED DESCRIPTION OF THE INVENTION

Figures 1, 2:
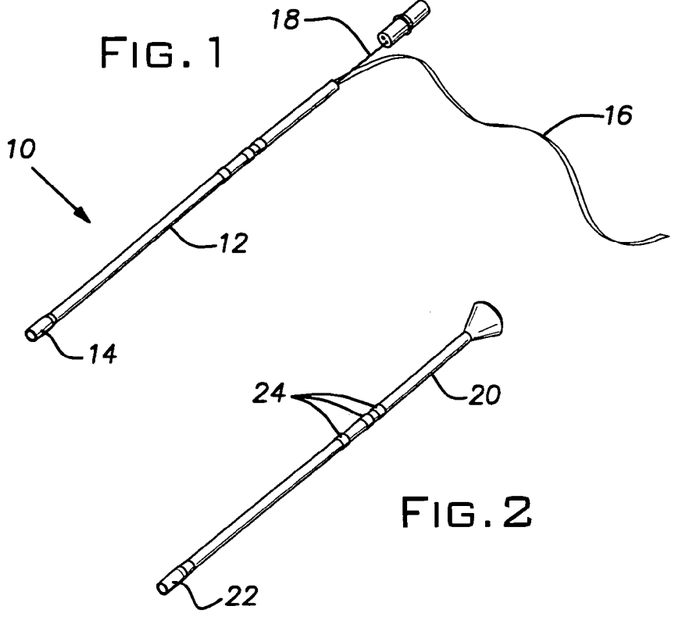
FIG. 1 is a perspective view of the first embodiment of the present invention in its assembled form.
FIG. 2 is a perspective view of the retrieving member.

Referring now to the drawings, FIG. 1 shows a first embodiment of the bridle catheter 10 in its final assembled state. The bridle catheter 10 includes a flexible member 12, a magnet 14, a tape portion 16, and a rod 18. FIG. 2 shows the retrieving member 20 used to retrieve the flexible member 12 while in the patient's nostril. The retrieving member 20 further includes a magnetic distal end 22 and a plurality of indicating marks 24. The indicating marks 24 are used to measure the depth the retrieving member 20 as it is inserted into the patient's nostril so as to prevent unnecessary contact of the retrieving member 20 within the patient. The procedure for retrieving the flexible member 12 with the retrieving member 20 and therefore placing the bridle catheter 10 in the patient will be described in more detail below.

Figures 3, 4, 5:
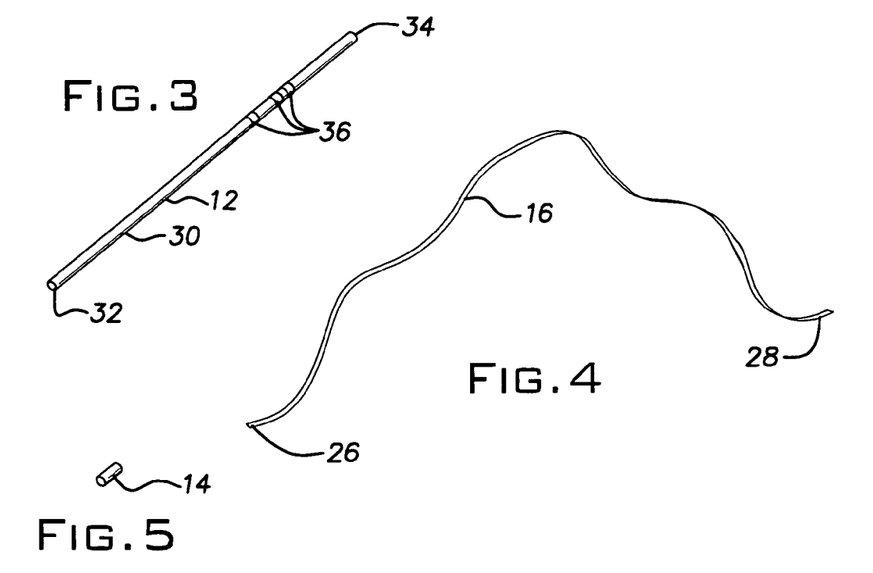
FIG. 3 is a perspective view of the flexible member.
FIG. 4 is a perspective view of the tape portion.
FIG. 5 is a perspective view of the magnet for insertion into the first end of the flexible member.

Referring to FIGS. 3-5, the components of the bridle catheter will now be described. The flexible member 12 further consists of a flexible tube 30 having a first 32 and second end 34. The flexible member 12 can be made with any type of flexible material commonly known in the art and chosen with sound engineering judgment. In the preferred embodiment the flexible member 12 is made out of silicone. The flexible member 12 further consists of a plurality indicating marks 36 that measure the depth the flexible member 12 as it is inserted into the patient's nostril so as to prevent unnecessary contact in the patient. The tape portion 16 further consists of a first 26 and second end 28. The tape portion 16 can be any type of string like material suitable for insertion into a patient that is commonly known in the art and chosen with sound engineering judgment. In the preferred embodiment the tape portion 16 is umbilical tape. The magnet 14 is a powerful rare earth type magnet and is secured in the first end 32 of the flexible member 12 as will be subsequently described.

Figures 6, 7, 8, 9:
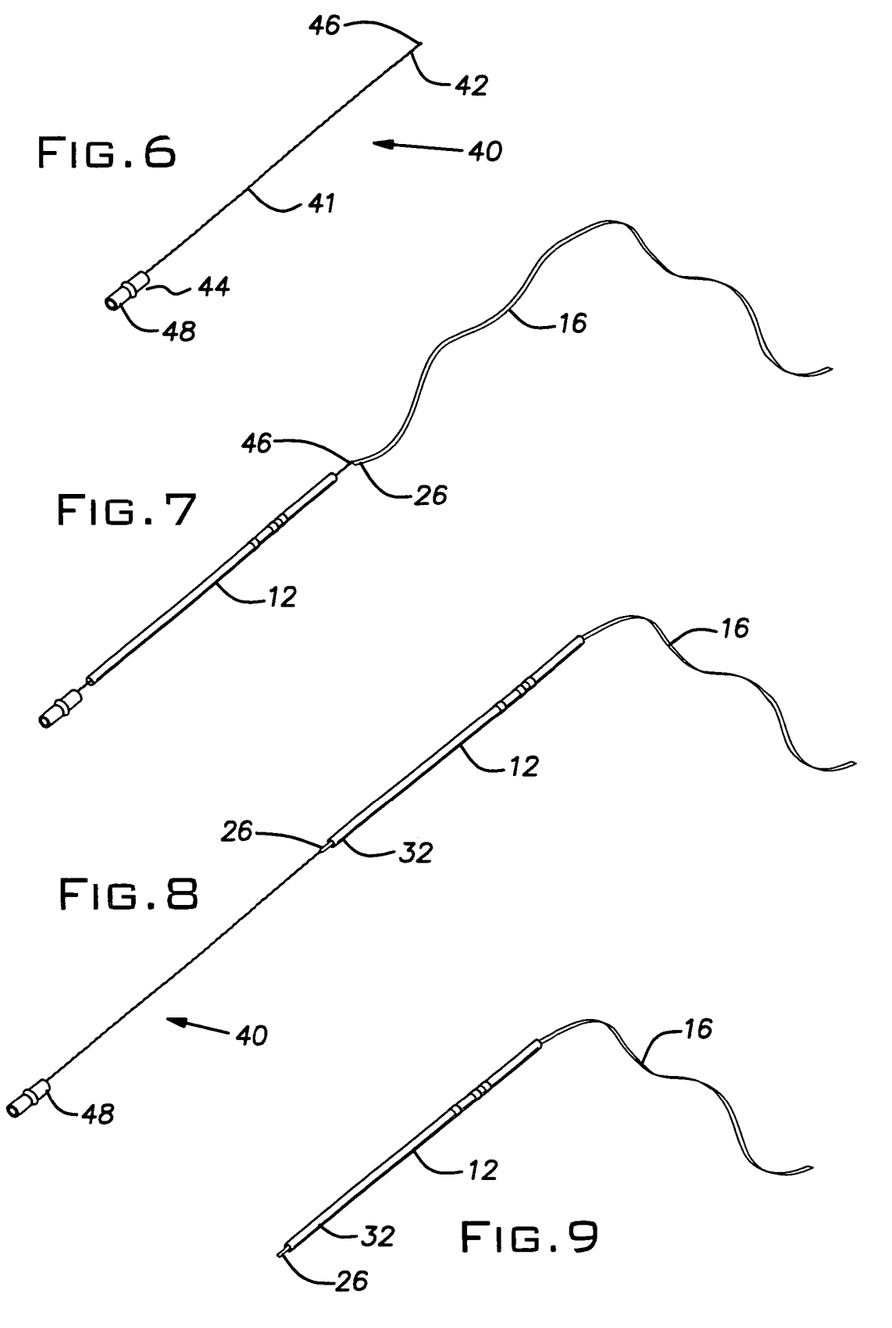
FIG. 6 is a perspective view of the guide used to thread the tape portion into the flexible member.
FIG. 7 is a perspective view showing the guide inserted into the flexible member and attachment of the tape portion to the first end of the guide.
FIG. 8 is a perspective view showing the guide threading the tape portion through the flexible member.
FIG. 9 is a perspective view showing the tape portion threaded through the flexible member.
Figures 10, 11:
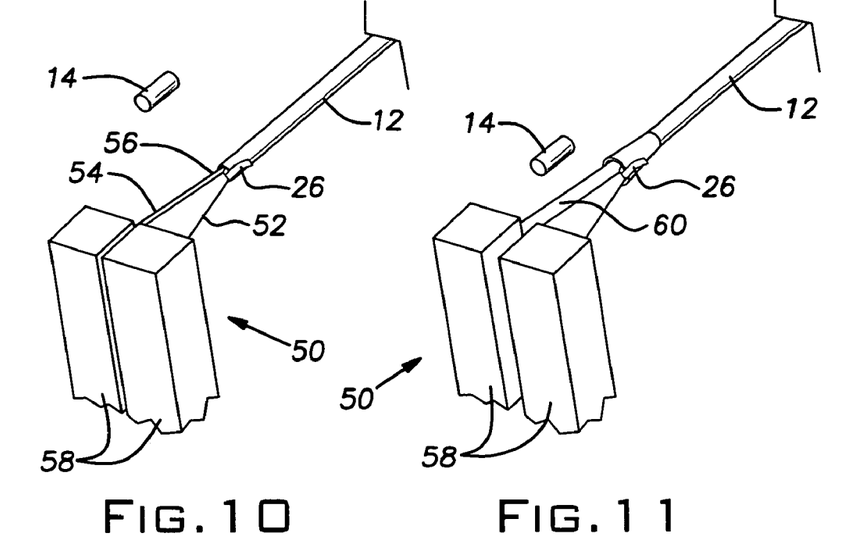
FIG. 10 is a perspective view showing the tube stretcher in a closed position inserted into the first end of the flexible member.
FIG. 11 is a perspective view showing the tube stretcher in an open position to allow insertion of the magnet into the first end of the flexible member.
Figures 12, 13:
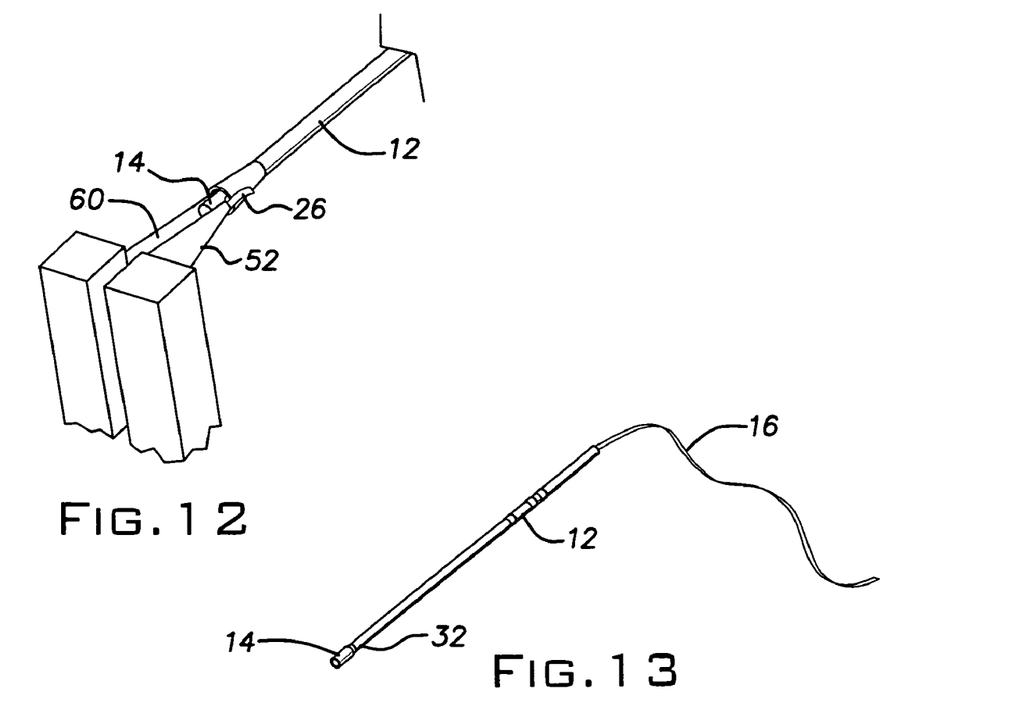
FIG. 12 is a perspective view showing the magnet placed in the open tube stretcher.
FIG. 13 is a perspective view showing the magnet and the tape portion secured in the first end of the flexible member.

Referring to FIGS. 6-13, assembly of the first embodiment of the bridle catheter 10 will now be described. FIG. 6 shows a guide 40 consisting of a wire 41 having a first 42 and second end 44. The first end 42 further consists of an attachment means 46 to attach the first end 26 of the tape portion 16 to the guide 40. Attached to the second end 44 of the wire 41 is a handle or knob 48 used to grasp the guide 40 during the assembly process. As shown in FIG. 7 the first end 42 of the guide is inserted into the first end 32 of the flexible member 12 until the first end 42 of the guide 40 extends beyond the second end 34 of the flexible member 12. The first end 26 of the tape portion 16 is then attached to the first end 42 of the guide 40 and threaded through the flexible member 12 as shown in FIG. 8. The guide 40 is then detached from the first end 26 of the tape portion 16 leaving a small portion of the tape portion 16 extending past the first end 32 of the flexible member 12 as shown in FIG. 9. Referring to FIGS. 10-13 insertion of the tube stretcher 50 will now be described. The tube stretcher 50 consists of a plurality of conical shaped fingers 52 having a proximal 54 and a distal end 56. The diameter of each finger 52 decreases as the finger 52 extends from the proximal end 54 to the distal end 56. The proximal end 54 of each finger 52 is attached to a separate plank 58. It should be noted that the fingers 52 and the planks 58 can be manufactured from a single piece of material therefore comprising an integrated device. The planks 58 are biased to a closed position so the distal end 56 of the fingers 52 are biased in a closed position and can be inserted into the first end 32 of the flexible member 12 as shown in FIG. 10. Referring to FIG. 11 the tube stretcher 50 stretches the first end 32 of the flexible member 12 by separating the planks 58 thereby causing the fingers 52 to separate. Operation of the tube stretcher from a closed position to an open position is commonly known in the art and will not be described herein. A gap 60 is formed between the fingers 52 to allow insertion of the magnet 14 as shown in FIGS. 11 and 12. Referring to FIG. 13, after the magnet 14 is inserted between the fingers 52 and into the first end 32 of the flexible member 12 the tube stretcher 50 is removed and the magnet 14 is now securely positioned in the first end 32 of the flexible member 12. Furthermore, the first end 26 of the tape portion 16 is securely positioned between the magnet 14 and the first end 32 of the flexible member 12. Any excess portion of the tape portion 16 is either trimmed off or pulled back so the first end 26 of the tape portion 16 is flush with the first end 32 of the flexible member 12. Finally, as shown in FIG. 1 the rod 18 is inserted into the second end 34 of the flexible member 12 to provide a degree of stiffness to facilitate insertion of the flexible member 12 into the patient's nostril.

Figures 14, 14A:
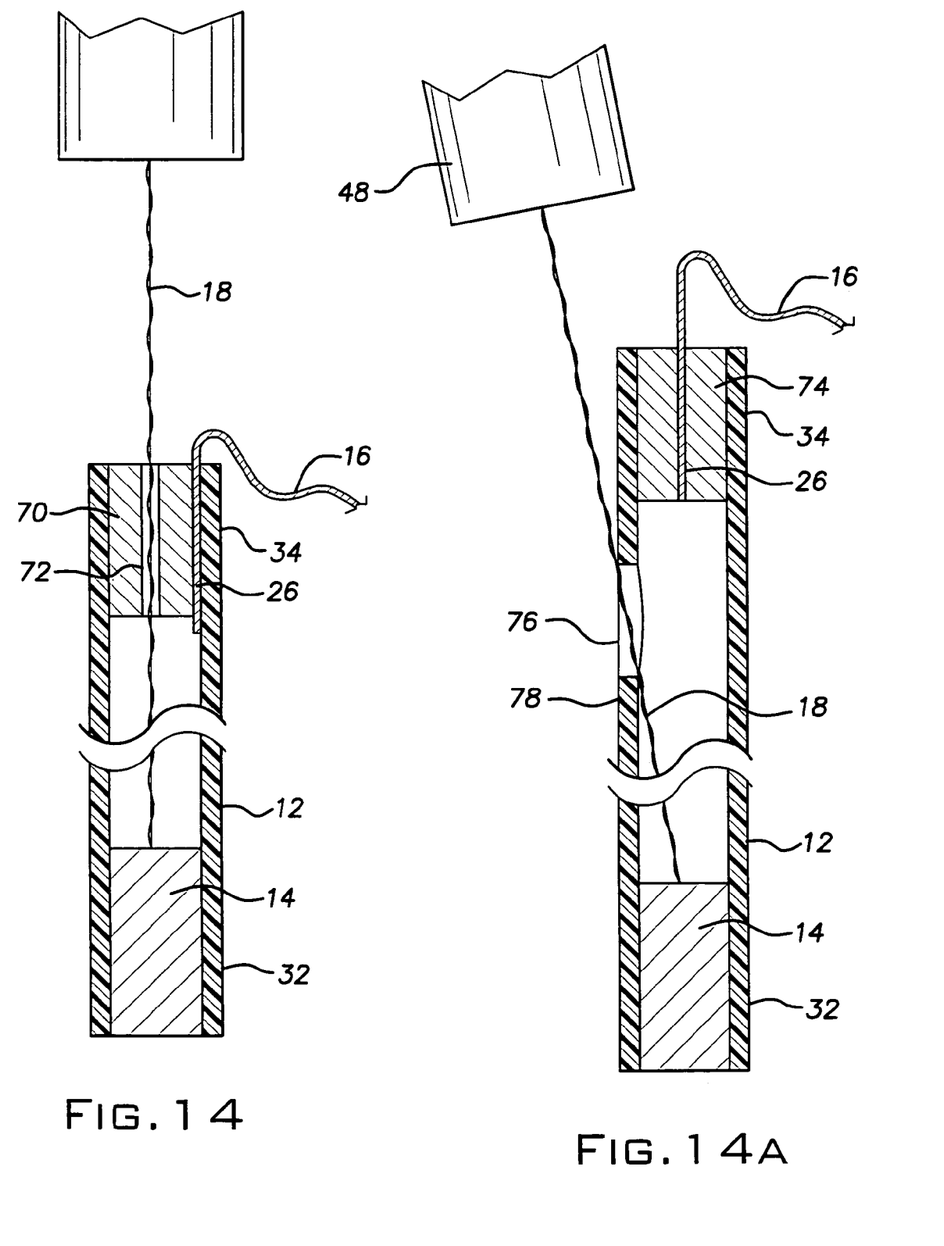
FIG. 14 is a perspective view showing a second embodiment of the present invention.
FIG. 14a is a perspective view of a third embodiment of the present invention.

FIG. 14 shows a second embodiment of the present invention. In this embodiment a plug 70 having an aperture 72 that extends the length of the plug 70 is inserted into the second end 34 of the flexible member 12 in the same manner that the magnet 14 is inserted into the flexible member 12 in the first embodiment. The plug 70 secures the first end 26 of the tape portion 16 between the plug 70 and the second end 34 of the flexible member 12. Therefore, in this embodiment the tape portion 16 is not threaded through the flexible member 12 as in the first embodiment. In this embodiment a small portion of the tape portion 16 is simply inserted into the second end 34 of the flexible member 12 and is secured by the plug 70. The magnet 14 is inserted into the first end 32 of the flexible member 12 in the same manner as in the first embodiment and will not be repeated. Finally, the rod 18 is inserted through the aperture 72 in the plug 70 and into the flexible member as shown in FIG. 14.

FIG. 14a shows a third embodiment of the present invention. In this embodiment an adhesive 74 such as glue is used to secure the first end 26 of the tape portion 16 to the second end 34 of the flexible member 12 in a manner commonly known in the art. The magnet 14 is inserted into the first end 32 of the flexible member 12 in the same manner as in the first embodiment and will not be repeated. An aperture 76 may be provided in the sidewall 78 of the flexible member 12 adjacent to the adhesive 74 to permit insertion of the rod 18.

Figure 15:
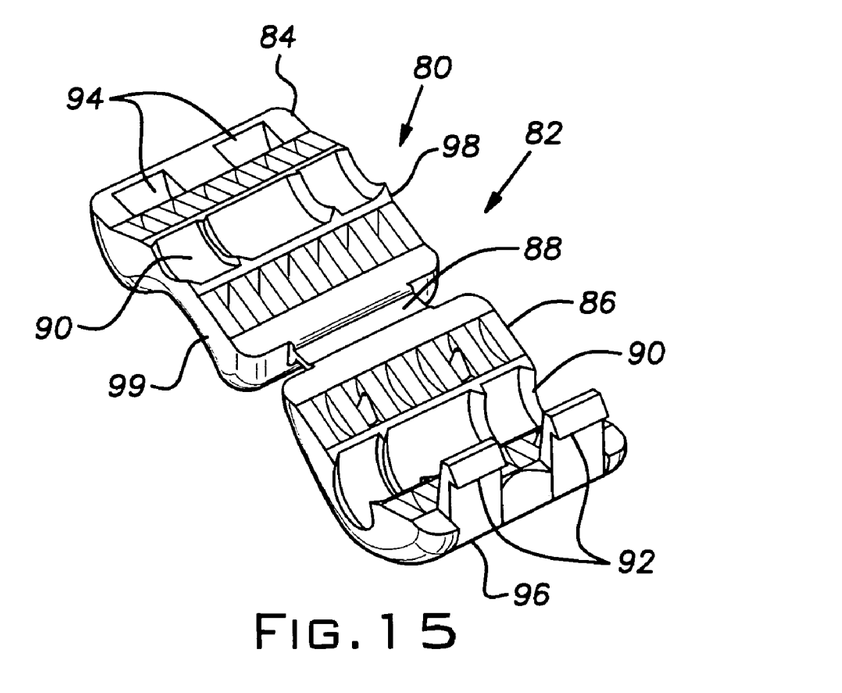
FIG. 15 is a perspective view of the fastening means in the open position.
Figure 16:
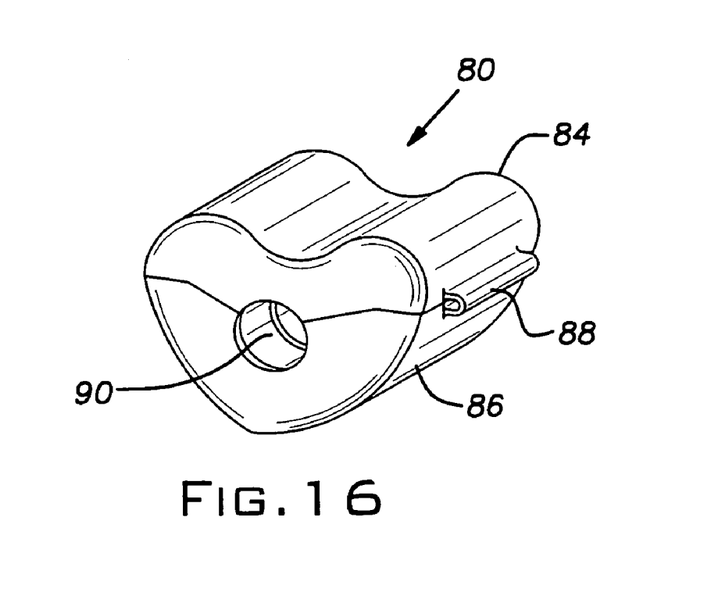
FIG. 16 is a perspective view of the fastening means in the closed position.
Figure 17A:
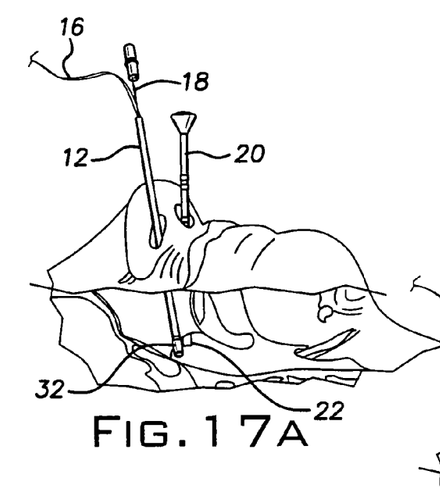
FIG. 17a is a perspective view showing how the flexible member and the retrieving member are inserted to the patient's nostrils.
Figure 17B:
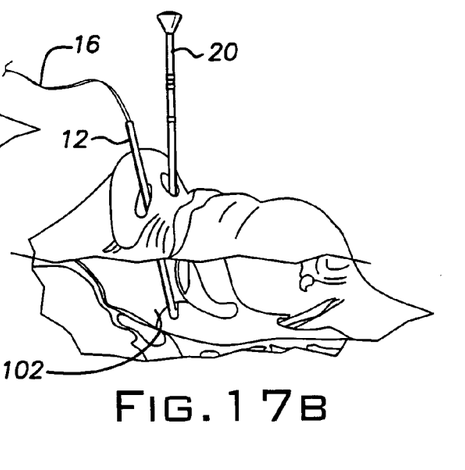
FIG. 17b is a perspective view showing retrieval of the flexible member.
Figure 17C:
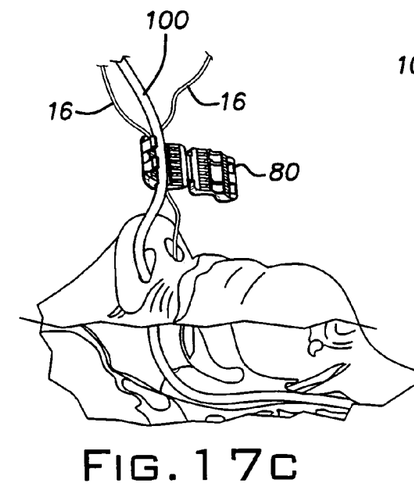
FIG. 17c is a perspective view showing the tape portion in the patient after the flexible member has been removed and attachment of the fastening means.
Figure 17D:
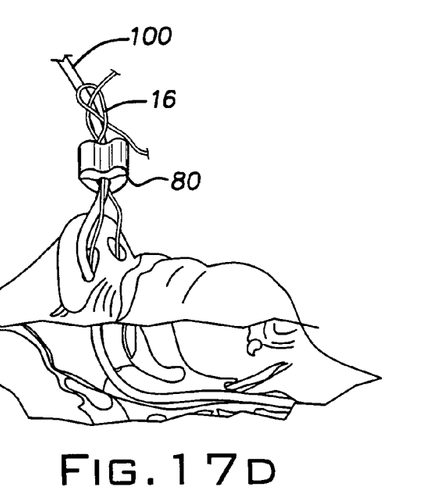
FIG. 17d is a perspective view of the tape portion after placement in the patient and securing the tape portion and nasal tube with the fastening means.

Referring to FIGS. 15 and 16, the present invention further consists of a fastening means 80. The fastening means 80 secures the nasal tube and the tape portion 16 in place after the bridle 10 is placed in the patient as will be described below. The fastening means can be any type of fastener chosen with sound engineering judgment such as a clip, clasp, clamp, buckle and the like. In the preferred embodiment the fastening means 80 consists of a clip 82. The clip 82 consists of a first side 84, a second side 86 and connecting member 88 that integrally connects the first 84 and second 86 sides. The first 84 and second 86 side each contain at least one channel 90 that extends from the top 98 to the bottom 99 of each side 84, 86. It should be noted that each side may contain multiple channels chosen with sound engineering judgment. In the preferred embodiment each side 84, 86 contains one channel 90. The channel 90 receives and secures the nasal tube and the tape portion 16 in place when in the closed position. The clip 82 further consists of a plurality of latches 92 positioned on the outer portion 96 of either side 84, 86. Mating holes 94 are positioned on the side 84, 86 opposite the latches 92 and receive the latches 92 when the clip 82 is in the closed position as shown in FIG. 16.

Referring to FIGS. 17a-17d, placing the bridle catheter 10 into the patient will now be described. The first end 32 of the flexible member 12 is inserted into the first nostril of the patient and is extended down to the posterior nasopharynx (not shown). The magnetic distal end 22 of the retrieving member 20 is inserted into the second nostril and is also extended down to the posterior nasopharynx. As the retrieving member 20 reaches the posterior nasopharynx the magnetic distal end 22 attracts the magnet 14 located in the first end 32 of the flexible member 12 causing the two magnetic ends to connect or snap together. The rod 18 is then removed from the flexible member 12 and the retrieving member 20 is pulled out of the second nostril thereby pulling the flexible member 12 through the patient's nose and out the second nostril until only the tape portion 16 remains in the patient. The flexible member 12 is then cut away from the tape portion 16 thereby leaving the tape portion 16 threaded through both nostrils of the patient forming a loop around the vomer bone 102. The ends of the tape portion 16 and the nasal tube 100 are then placed into a channel 90 in either side 84, 86 of the clip 82. The clip 82 is closed and snapped together by inserting the latches 92 into the mating holes 94 thereby securing the nasal tube 100 to the tape portion 16. If desired the ends of the tape portion 16 can be tied off for additional security.

While specific embodiments of the invention have been described and illustrated, it is to be understood that these embodiments are provided by way of example only and that the invention is not to be construed as being limited thereto but only by proper scope of the following claims.

What is claimed is:

1. A nasal tube retaining system comprising:
    a flexible member having a first and second end, wherein the first end is inserted into a first nostril of a patient, the flexible member having sufficient flexibility to form a loop about a vomer bone of said patient;
    a magnet operatively attached in the first end of the flexible member, the magnet being inserted a distance into the first end of the flexible member and secured therein so as to inhibit movement of the magnet relative to the first end of the flexible member;
    a tape portion having a first and second end, wherein the tape portion is operatively attached to the flexible member;
    a retrieving member having a magnetic distal end, wherein the distal end is inserted into a second nostril of the patient, wherein the distal end of the retrieving member attracts the first end of the flexible member to retrieve and remove the flexible member out of the second nostril; and,
    a fastening means to secure at least one nasal tube and the first and second ends of the tape portion.

2. The nasal tube retaining system of claim 1, wherein the first end of the tape portion is threaded through the flexible member and is secured between the magnet and the first end of the flexible member.

3. The nasal tube retaining system of claim 1 further comprising:
    a securing means operatively attached to the second end of the flexible member,
    wherein the securing means secures the first end of the tape portion to the second end of the flexible member.

4. The nasal tube retaining system of claim 3, wherein the securing means further comprises a plug having an aperture.

5. The nasal tube retaining system of claim 3 further comprising:
    an aperture in the sidewall of the flexible member adjacent to the securing means; and,
    wherein the securing means further comprises an adhesive.

6. The nasal tube retaining system of claim 1 further comprising:
    a rod for insertion into the flexible member to assist insertion of the flexible member into the nostril.

7. The nasal tube retaining system of claim 1, wherein the flexible member and the retrieving member further comprise at least one indicator mark.

8. The nasal tube retaining system of claim 1, wherein the fastening means is a clip having a first and second portions and a hinge portion operatively connecting the first and second portions.

9. The nasal tube retaining system of claim 8, wherein the first and second portions of the clip further comprise at least one channel for receiving at least one nasal tube and the first and second ends of the tape portion.

10. A method of placing a nasal tube retaining system into a patient comprising the steps of:
providing a flexible member having a first and second end, a magnet operatively attached in the first end of the flexible member, a tape portion having a first and second end, wherein the tape portion is operatively attached to the flexible member, a rod inserted into the flexible member, a retrieving member having a magnetic distal end;
inserting the first end of the flexible member into a first nostril of the patient;
extending the flexible member down to the posterior nasopharynx;
inserting the distal end of the retrieving member into a second nostril of the patient;
extending the retrieving member down to the posterior nasopharynx thereby permitting the first end of the flexible member and the distal end of the retrieving member to magnetically connect;
removing the rod from the flexible member;
pulling the retrieving member out of the second nostril thereby removing the flexible member out of the second nostril until the flexible member is completely removed from the patient leaving only the tape portion remaining in the patient;
cutting the flexible member; and,
removing the flexible member from the tape portion.

11. The method of claim 10 further comprising the steps of:
providing a fastening means having a first and second portion, a hinge portion connecting the first and second portions, a channel in the first and second portion;
placing a nasal tube and the first and second ends of the tape portion into the channel of either the first or second portion; and,
closing the fastening means thereby securing the nasal tube and the tape portion in the fastening means.

12. A method of packaging a nasal tube retaining system comprising the steps of:
providing a flexible member having a first and second end, a magnet for attachment in the first end of the flexible member, a tape portion having a first and second end, and a tube stretcher, the flexible member having a sufficient flexibility to form a loop about a vomer bone of a patient;
stretching the first end of the flexible member to increase an interior cross-sectional area of the first end of the flexible member;
inserting the magnet into the first end of the flexible member such that the magnet extends a distance within the flexible member;
securing the magnet in the first end of the flexible member so as to inhibit movement of the magnet relative to the first end of the flexible member; and,
securing the tape portion to the flexible member, wherein the step of securing the magnet is independent of the step of securing the tape portion.

13. The method of claim 12 further comprising the steps of:
providing a guide having a first end;
wherein prior to the step of stretching the first end of the flexible member the method further comprises:
inserting the guide into the first end of the flexible member and through the flexible member;
attaching the first end of the tape to the first end of the guide;
pulling the guide out of the flexible member thereby pulling the tape portion through the flexible member; and,
wherein the first end of the tape portion is secured between the magnet and the first end of the flexible member.

14. The method of claim 13 further comprising:
providing a rod having a first end; and,
inserting the first end of the rod into the second end of the flexible member until the first end of the rod contacts the magnet.

15. The method of claim 12 further comprising the steps of:
providing a plug having an aperture;
wherein prior to the step of stretching the first end of the flexible member the method further comprises:
stretching the second end of the flexible member;
inserting the plug into the second end of the flexible member; and,
wherein the first end of the tape portion is secured between the plug and the second end of the flexible member.

16. The method of claim 15 further comprising:
providing a rod having a first end; and,
inserting the first end of the rod into the aperture of the plug and into the flexible member until the first end of the rod contacts the magnet.

* * * * *